United States Patent [19]

Rainer

[11] Patent Number: 5,719,161

[45] Date of Patent: Feb. 17, 1998

[54] ALKOXY ALKYL CARBAMATES OF IMIDAZO(1.2-A)PYRIDINES

[75] Inventor: Georg Rainer, Constance, Germany

[73] Assignee: BYK Gulden Lomberg Chemische Fabrik GmbH, Constance, Germany

[21] Appl. No.: 624,525

[22] PCT Filed: Oct. 8, 1994

[86] PCT No.: PCT/EP94/03326

§ 371 Date: Jun. 24, 1996

§ 102(e) Date: Jun. 24, 1996

[87] PCT Pub. No.: WO95/10518

PCT Pub. Date: Apr. 20, 1995

[30] Foreign Application Priority Data

Oct. 11, 1993 [CH] Switzerland .................... 3047/93

[51] Int. Cl.[6] .................. A61C 31/485; C07D 471/04
[52] U.S. Cl. .................. 514/300; 546/121
[58] Field of Search .................. 546/121; 514/300

[56] References Cited

U.S. PATENT DOCUMENTS

| 4,831,041 | 5/1989 | Shiokawa | 514/300 |
| 4,920,129 | 4/1990 | Shiokawa | 514/300 |

FOREIGN PATENT DOCUMENTS

| 033094 | 8/1981 | European Pat. Off. . |
| 0204285 | 10/1986 | European Pat. Off. . |
| 0266890 | 10/1986 | European Pat. Off. . |
| 0228006 | 8/1987 | European Pat. Off. . |

*Primary Examiner*—Alan L. Rotman
*Assistant Examiner*—Evelyn Huang
*Attorney, Agent, or Firm*—Jacobson, Price, Holman & Stern, PLLC

[57] ABSTRACT

This invention relates to novel compounds of formula (I) and their therapeutic use in the treatment of gastrointestinal diseases.

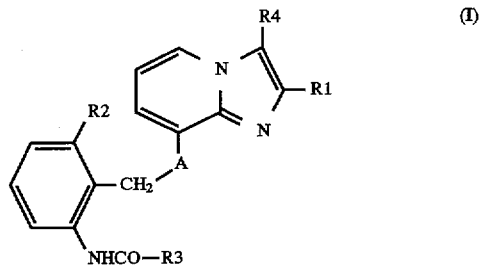

9 Claims, No Drawings

ALKOXY ALKYL CARBAMATES OF IMIDAZO(1.2-A)PYRIDINES

This application is the national phase of PCT/EP94/03326 filed Oct. 8, 1994.

FIELD OF APPLICATION OF THE INVENTION

The invention relates to novel compounds which are intended for use in the pharmaceutical industry as active compounds for the production of medicaments.

KNOWN TECHNICAL BACKGROUND

European Patent Application EP-A-0,033,094 describes imidazo[1,2-a]pyridines which in the 8-position carry an aryl substituent which is preferably a phenyl radical, thienyl radical, pyridyl radical or a phenyl radical substituted by chlorine, fluorine, methyl, tert-butyl, trifluoromethyl, methoxy or cyano. Aryl radicals of particular interest mentioned in EP-A-0,033,094 are the radicals phenyl, o- or p-fluorophenyl, p-chlorophenyl and 2,4,6-trimethylphenyl, of which the radicals phenyl, o- or p-fluorophenyl and 2,4,6-trimethylphenyl are particularly preferred.—European Patent Applications EP-A-0,204,285, EP-A-0,228,006, EP-A-0,268,989 and EP-A-0,308,917 describe imidazo[1,2-a]pyridines which in the 3-position carry an unsaturated aliphatic radical, in particular a (substituted) alkynyl radical.—European Patent Application EP-A-0,266,890 describes imidazo-[1,2-a]pyridines which are substituted in the 8-position by an alkenyl, alkyl or cycloalkylalkyl radical.

DESCRIPTION OF THE INVENTION

It has now been found that the compounds described below in greater detail, which differ from the compounds of the prior art, in particular, by the substitution in the 3- or in the 8-position, have surprising and particularly advantageous properties.

The inventions [sic] relate to compounds of the formula I (see attached formula sheet), in which
R1 is 1-4C-alkyl,
R2 is 1-4C-alkyl,
R3 is 1-4C-alkoxy-2-4C-alkoxy,
R4 is 1-4C-alkyl or hydroxymethyl and
A is O (oxygen) or NH,
and their salts.

1-4C-Alkyl is straight-chain or branched alkyl radicals having 1 to 4 carbon atoms. Examples which may be mentioned are the butyl, isobutyl, sec-butyl, tert-butyl, propyl, isopropyl, ethyl and, in particular, the methyl radical.

1-4C-Alkoxy is an oxygen atom to which one of the abovementioned 1-4C-alkyl radicals is bonded. The methoxy radical is preferred. 2-4C-Alkoxy is an oxygen atom to which a 2-4C-alkyl radical (selected from the abovementioned 1-4C-alkyl radicals) is bonded. 1-4C-Alkoxy-2-4C-alkoxy is a 2-4C-alkoxy radical to which a 1-4C-alkoxy radical is bonded. The 2-methoxyethoxy radical is preferred.

Suitable salts of compounds of the formula I are preferably all acid addition salts. Particular mention may be made of the pharmacologically tolerable salts of the inorganic and organic acids customarily used in pharmacy. Pharmacologically intolerable salts, which may be initially obtained as process products, for example in the preparation of the compounds according to the invention on an industrial scale, are converted into pharmacologically tolerable salts by processes known to the person skilled in the art. Those suitable are water-soluble and water-insoluble acid addition salts with acids, for example hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, burytic acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, where the acids are employed in salt preparation—depending on whether a mono- or polybasic acid is concerned and on which salt is desired—in an equimolar quantitative ratio or one differing therefrom.

Exemplary compounds which may be mentioned are the compounds 8-{2-[(2-methoxyethoxy)carbonylamino]-6-methylbenzyloxy}-2-methylimidazo[1,2-a]pyridine-3-methanol, 8-{2-[(2-methoxyethoxy)carbonylamino]-6-methylbenzylamino}-2-methylimidazo[1,2-a]pyridine-3-methanol and 8-{2-[(2-methoxyethoxy) carbonylamino]-6-methylbenzyl-amino}-2,3-dimethylimidazo[1,2-a]pyridine, and their salts.

To be emphasized are those compounds of the formula I in which R4 is hydroxymethyl and A is O (oxygen) and R1, R2 and R3 have the meanings indicated above, and their salts.

The invention further relates to a process for the preparation of the compounds of the formula I and their salts. The process is characterized in that a) compounds of the formula II (see the attached formula sheet), in which R1, R4 and A have the meanings indicated above, or their salts, are reacted with compounds of the formula III (see attached formula sheet), in which R2 and R3 have the meanings indicated above and X is a suitable reactive leaving group, or their salts, or in that b) for the preparation of compounds of the formula I in which R4 is hydroxymethyl, compounds of the formula IV (see attached formula sheet), in which R1, R2, R3 and A have the meanings indicated above, are reduced and in that, if desired, the compounds I obtained according to a) or b) are then converted into their salts, or in that, if desired, the compounds I are then liberated from salts of the compounds I obtained.

The reaction of the compounds II with the compounds III is carried out in a manner familiar per se to the person skilled in the art. A suitable reactive leaving group is, for example, a halogen atom (preferably chlorine or bromine) or a methanesulphonyloxy group. The reaction is advantageously carried out in the presence of a base (e.g. of an inorganic hydroxide, such as sodium hydroxide, or of an inorganic carbonate, such as potassium carbonate, or of an organic nitrogen base, such as triethylamine, pyridine, collidine, or 4-dimethylamino(pyridine), where the carrying-out of the reaction can be favoured by addition of catalysts, such as alkali metal iodide or tetrabutylammonium bromide.

The reduction of the compounds IV is performed in a manner customary per se to the person skilled in the art. It is carried out in inert solvents, e.g. lower aliphatic alcohols, e.g. using suitable hydrides, for example sodium borohydride, if desired with the addition of water.

The person skilled in the art is familiar on account of his expert knowledge with the reaction conditions which are specifically necessary for carrying out the process.

The isolation and purification of the substances according to the invention is carried out in a manner known per se, for example, by distilling off the solvent in vacuo and recrystallizing the resulting residue from a suitable solvent or subjecting it to one of the customary purification methods, for example column chromatography on suitable support material.

Acid addition salts are obtained by dissolving the free base in a suitable solvent, e.g. in a chlorinated hydrocarbon, such as methylene chloride or chloroform, a lower molecular weight aliphatic alcohol (ethanol, isopropanol), a ketone, such as acetone, or an ether, such as THF or diisopropyl ether, which contains the desired acid, or to which the desired acid is then added.

The salts are obtained by filtration, reprecipitation, precipitation with a non-solvent for the addition salt or by evaporation of the solvent. Salts obtained can be converted by basification, e.g. with aqueous ammonia solution, into the free bases which can in turn be converted into acid addition salts. In this manner, pharmacologically intolerable acid addition salts can be converted into pharmacologically tolerable acid addition salts.

The starting compounds II are disclosed, inter alia, in European Patent Applications EP-A-0,290,003 and EP-A-0, 299,470. The starting compounds III are novel. They are prepared analogously to processes known from the literature, by converting the hydroxy group in compounds III where X=OH into a reactive leaving group, e.g. into a halogen atom, by reaction with a halogenating agent, e.g. thionyl chloride, thionyl bromide, phosphorus tribromide or oxalyl chloride, or into a methanesulphonyloxy group, by reaction with methanesulphonyl chloride, if desired in the presence of a base.

The compounds IV are novel and likewise a subject of the invention. They are prepared like the compounds of the formula I by analogous reaction of compounds II where R4=CHO with compounds III as described above.

The following examples serve to explain the process for the preparation of the compounds I in greater detail. The abbreviation RT stands for room temperature, h stands for hour(s).

EXAMPLES

Final and Intermediate Products 1. 8-{2-[(2-Methoxyethoxy) carbonylamino]-6-methylbenzyloxy}-2-methylimidazo[1,2-a]pyridine-3-carboxaldehyde A mixture of 2.0 g (11.35 mmol) of 8-hydroxy-2-methylimidazo[1,2-a]pyridine-3-carboxaldehyde, 1.2 g of anhydrous sodium carbonate, 0.17 g (1.14 mmol) of sodium iodide and 3.3 g (12.8 mmol) of 2-methoxyethyl 2-chloromethyl-3-methylphenylcarbamate in 30 ml of acetone is stirred at RT for 24 h and poured onto 200 ml of ice-water. The precipitate is filtered off, dried and recrystallized from toluene/diisopropyl ether. 3.9 g (86.5%) of the title compound of m.p. 119°–120° C. are obtained.

8-{2-[(2-Methoxyethoxy)carbonylamino]-6-methylbenzyloxy}-2-methylimidazo[1,2-a]pyridine-3-methanol A suspension of 3.7 g (9.3 mmol) of 8-{2-[(2-methoxyethoxy)carbonylamino]-6-methylbenzyloxy}-2-methylimidazo[1,2-a]pyridine-3-carboxaldehyde in 40 ml of methanol is treated at RT with 362 mg (9.3 mmol) of 97% sodium borohydride and stirred for 75 min. It is added to ice/water, extracted with dichloromethane and concentrated in a Rotavapor. The residual oil is crystallized using 5 ml of isopropyl alcohol, 5 ml of toluene and diisopropyl ether. 2.7 g (72.7%) of the title compound of m.p. 121°–123° C. are obtained.

3. 8-{2-[(2-Methoxyethoxy)carbonylamino]-6-methylbenzylamino}-2-methylimidazo[1,2-a]pyridine-3-carboxaldehyde A mixture of 2.0 g (11.41 mmol) of 8-amino-2-methylimidazo[1,2-a]pyridine-3-carboxaldehyde, 1.21 g (11.41 mmol) of anhydrous sodium carbonate, 0.17 g (1.14 mmol) of sodium iodide and 3.5 g (13.6 mmol) of 2-methoxyethyl 2-chloromethyl-3-methylphenylcarbamate in 30 ml of acetone is stirred at RT for 24 h and concentrated in a Rotavapor. The residue is treated with 100 ml of water and extracted with ethyl acetate, and the organic phase is dried with magnesium sulphate and concentrated in vacuo. The residue is recrystallized from toluene. 3.31 g (73%) of the title compound of m.p. 153°–155° C. are obtained.

4. 8-{2-[(2-Methoxyethoxy)carbonylamino]-6-methylbenzylamino}-2-methylimidazo[1,2-a]pyridine-3-methanol 2.8 g (7.06 mmol) of 8-{2-[(2-methoxyethoxy)carbonylamino]-6-methylbenzylamino}-2-methylimidazo[1,2-a]-pyridine-3-carboxaldehyde are reduced with sodium borohydride analogously to Example 2, methanol is distilled off in vacuo, and the residue is treated with water and ethyl acetate and adjusted to pH 9 using potassium hydrogen phosphate solution. The mixture is extracted several times with ethyl acetate, dried and concentrated in vacuo, and the residue is recrystallized from toluene/diisopropyl ether. 2.28 g (81%) of the title compound of m.p. 138°–140° C. are obtained.

5. 8-{2-[(2-Methoxyethoxy)carbonylamino]-6-methylbenzylamino}-2,3-dimethylimidazo[1,2-a]pyridineisopropyl alcohol (1/1)

A mixture of 3.0 g (18.6 mmol) of 8-amino-2,3-dimethylimidazo[1,2-a]pyridine, 4.9 g (46.2 mmol) of anhydrous sodium carbonate, 0.28 g (1.86 mmol) of sodium iodide and 5.8 g (22.5 mmol) of 2-methoxyethyl 2-chloromethyl-3-methylphenylcarbamate in 30 ml of acetone is stirred at RT for 20 h. It is filtered and concentrated in vacuo, and the residue is treated with water and ethyl acetate, adjusted to pH 6 using dilute hydrochloric acid and extracted with ethyl acetate. The organic solution is dried and concentrated in vacuo. The residue is treated with 40 ml of acetone and treated with a solution of 1.2 g (10..3 mmol) of fumaric acid in 80 ml of acetone. No crystallization takes place. Therefore the reconcentrated solution is treated with toluene and isopropyl alcohol and 4.9 g of a fumarate are precipitated at 0° C. using diisopropyl ether. This is treated with 50 ml of ethyl acetate and 10 ml of water, the mixture is adjusted to pH 9 using sodium hydroxide solution and the free base is extracted with ethyl acetate. After concentrating in vacuo, the residue is dissolved in toluene/isopropyl alcohol and precipitated at 0° C. using petroleum ether (b.p. 40° C.). 2.2 g (26.7%) of the title compound of m.p. 85°–86° C. are obtained.

6. 8-{2-[(2-Methoxyethoxy)carbonylamino]-6-methylbenzyloxy}-2-methylimidazo[1,2-a]pyridine-3-methanol A mixture of 178 mg (1.0 mmol) of 8-hydroxy-2-methylimidazo[1,2-a]pyridine-3-methanol, 117 mg (1.1 mmol) of anhydrous sodium carbonate, 15 mg (0.1 mmol) of sodium iodide and 283 mg (1.1 mmol) of 2-methoxyethyl 2-chloromethyl-3-methylphenylcarbamate in 5 ml of acetone is stirred at RT for 48 h, worked up analogously to Example 2 and chromatographed by means of ethyl acetate/isopropyl alcohol (9:1). 247 mg (62%) of the title compound are obtained.

7. 8-{2-[(2-Methoxyethoxy)carbonylamino]-6-methylbenzyloxy}-2,3-dimethylimidazo[1,2-a]pyridine Analogously to Example 5, 2.0 g (12.4 mmol) of 8-hydroxy-2,3-dimethylimidazo[1,2-a]pyridine, 3.6 g (13.9 mmol) of 2-methoxyethyl 2-chloromethyl-3-methylphenylcarbamate, 0.18 g of sodium iodide and 1.3 g of sodium carbonate are reacted in 30 ml of acetone. 1.07 g (22.5%) of the title compound of m.p. 107°–108° C. are obtained.

Starting Materials

A a. 2-Methoxyethyl 2-hydroxymethyl-3-methylphenylcarbamate

33.2 g (0.24 mol) of 2-methoxyethyl chloroformate are added dropwise at 10° C. with stirring and cooling to a solution of 33 g (0.24 mol) of 2-amino-6-methylbenzylalcohol and 19.4 ml (0.24 mol) of pyridine in 600 ml of isopropyl alcohol. The mixture is stirred at 0° C. for a further 2 h, treated with water and isopropyl acetate and extracted several times with isopropyl acetate. The organic phase is dried using magnesium sulphate and concentrated at 50° C. in a Rotavapor. The residue is chromatographed on a silica gel column by means of ethyl acetate. After concentrating in vacuo, 36 g (68%) of the title compound are obtained as an oil.

A b. 2-Methoxyethyl 2-chloromethyl-3-methylphenylcarbamate

9.4 g (0.079 mol) of thionyl chloride are added dropwise with stirring and cooling to a solution of 18.0 g (0.075 mol) of the preceding compound in 80 ml of toluene at 17°–20° C. and the mixture is allowed to stand at RT overnight. It is cooled in an ice bath and triturated and 11.2 g (57.7%) of the title compound of m.p. 100°–102° C. are obtained. By concentrating the mother liquor and crystallizing from toluene/petroleum ether (b.p. 40° C.), a second precipitate of 4.8 g (24.7%) having a similar melting point is obtained.

B. 8-Hydroxy-2-methylimidazo[1,2-a]pyridine-3-carboxaldehyde

4.77 g (0.02 mol) of 8-benzyloxy-2-methylimidazo[1,2-a]pyridine are stirred at 60° C. for 2.5 h in a Vilsmeier mixture of 20 ml of dimethylformamide and 2.3 ml of phosphorus oxychloride and the mixture is worked up in a customary manner using ice/water and potassium hydrogen carbonate. 8-Benzyloxy-2-methylimidazo[1,2-a]pyridine-3-carboxaldehyde of m.p. 105°–106° C. (from diisopropyl ether) is obtained. This compound is debenzylated analogously to Kaminski et al., J. Med. Chem. 28, 876 (1985), method H, to give the title compound of m.p. 251°–252° C.

Commercial Utility

The compounds of the formula I and their salts have useful pharmacological properties which make them commercially utilizable. In particular, they exhibit marked inhibition of gastric acid secretion and an excellent gastric and intestinal protective action in warm-blooded animals. In this connection, the compounds according to the invention are distinguished, in addition to good solubility in aqueous medium, by a high selectivity of action, a comparatively long duration of action, a good enteral activity, the absence of significant side effects and a wide therapeutic range.

"Gastric and intestinal protection" in this connection is understood as meaning the prevention and treatment of gastrointestinal diseases, in particular gastrointestinal inflammatory diseases and lesions (e.g. gastric ulcer, duodenal ulcer, gastritis, hyperacidic or medicament-related functional gastropathy) which can be caused, for example, by microorganisms (e.g. Helicobacter pylori), bacterial toxins, medicaments (e.g. certain anti-inflammatories and antirheumatics), chemicals (e.g. ethanol), gastric acid or stress situations. The compounds according to the invention in this connection also have an intrinsic action against the microorganism Helicobacter pylori.

In their excellent properties, the compounds according to the invention surprisingly prove clearly superior to the compounds known from the prior art in various models in which the antiulcerogenic and the antisecretory properties are determined. As a result of these properties, compounds of the formula I and their pharmacologically tolerable salts are outstandingly suitable for use in human and veterinary medicine, where they are used, in particular, for the treatment and/or prophylaxis of disorders of the stomach and/or intestine, but also for the treatment of osteoporosis.

The invention therefore further relates to the compounds according to the invention for use in the treatment and/or prophylaxis of the abovementioned.

Likewise, the invention comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention further relates to medicaments which contain one or more compounds of formula I and/or their pharmacologically tolerable salts.

The medicaments are prepared by processes which are known per se and familiar to the person skilled in the art. The pharmacologically active compounds according to the invention (=active compounds) are employed as medicaments either as such, or preferably in combination with suitable pharmaceutical auxiliaries and/or excipients in the form of tablets, coated tablets, capsules, suppositories, plasters (e.g. as TTS), emulsions, suspensions or solutions, the active compound content advantageously being between 0.1 and 95% and it being possible by the choice of the auxiliaries and excipients to obtain a pharmaceutical administration form (e.g. a sustained-release form or an enteric form) exactly tailored to the active compound and/or to the desired onset of action.

The auxiliaries or excipients which are suitable for the desired pharmaceutical formulations are familiar to the person skilled in the art on the basis of his expert knowledge. Tablet-coating compositions, antioxidants, dispersants, emulsifiers, antifoams, flavour corrigents, preservatives, solubilizers, colorants or, in particular, permeation promoters and complexing agents (e.g. cyclodextrins), for example, can be used in addition to solvents, gel formers, suppository bases, tablet auxiliaries and other active compound excipients.

The active compounds can be administered orally, parenterally or percutaneously.

In general, it has proved advantageous in human medicine to administer the active compound or active compounds in the case of oral administration in a daily dose of about 0.01 to about 20, preferably 0.05 to 5, in particular 0.1 to 1.5, mg/kg of body weight, if appropriate in the form of several, preferably 1 to 4, individual doses to achieve the desired result. In the case of parenteral treatment, similar or (in particular in the case of intravenous administration of the active compounds) generally lower doses can be used. Any person skilled in the art can easily fix the optimum dose and type of administration of the active compounds necessary in each case on the basis of his expert knowledge.

If the compounds and/or salts according to the invention are to be employed for the treatment of the abovementioned diseases, the pharmaceutical preparations can also contain one or more pharmacologically active constituents of other pharmaceutical groups, such as antacids,. for example aluminium hydroxide, magnesium aluminate; tranquillizers, such as benzodiazepines, for example diazepam; spasmolytics, e.g. bietamiverine, camylofin, anticholinergics, e.g. oxyphencyclimine, phencarbamide;

local anaesthetics, e.g. tetracaine, procaine; and if desired also enzymes, vitamins-or amino acids.

To be emphasized in this connection is in particular the combination of the compounds according to the invention with pharmaceuticals which inhibit acid secretion, for example $H_2$ blockers (e.g. cimetidine, ranitidine), $H^+/K^+$-ATPase inhibitors (e.g. omeprazole, pantoprazole), or further with so-called peripheral anticholinergics (e.g. pirenzepine, telenzepine) and also with gastrin antagonists with the aim of enhancing the main action in an additive or superadditive sense and/or eliminating or reducing the side effects, or further the combination with antibacterially active substances (e.g. cephalosporins, tetracyclines, nalidixic acid, penicillins or alternatively bismuth salts) for the control of Helicobacter pylori.

Pharmacology

The excellent gastric protective action and the gastric acid secretion-inhibiting action of the compounds according to the invention can be demonstrated in investigations on experimental animal models. The compounds according to the invention investigated in the model given below have been provided with numbers which correspond to the numbers of these compounds in the Examples.

Investigation of the Secretion-Inhibiting Effect on the Perfused Rat Stomach

Table 1 below shows the effect of the compounds according to the invention after intravenous administration on the acid secretion of the perfused rat stomach stimulated by pentagastrin in vivo.

TABLE 1

| No. | Dose (μmol/kg) i.v. | Maximum inhibition of acid secretion during the course of 3.5 h compared with value before in % |
|---|---|---|
| 2 | 1 | 97 |
| 4 | 1 | 83 |
| 5 | 1 | 80 |
| 7 | 1 | 92 |

Methodology

The abdomen of anaesthetized rats (CD rats, female, 200–250 g; 1.5 g/kg i.m. of urethane) was opened after tracheotomy by a median upper abdominal incision and a PVC catheter was fixed transorally in the oesophagus and a further one via the pylorus such that the ends of the tubes just projected into the stomach lumen. The catheter leading from the pylorus led outwards via a side opening in the right-hand abdominal wall.

After thorough irrigation (about 50–100 ml), a flow of warm physiological NaCl solution at 37° C. was continuously passed through the stomach (0.5 ml/min, pH 6.8–6.9; Braun-Unita I). The pH (pH meter 632, glass electrode EA 147; ∅–5 mm, Metrokm) was determined in the effluent collected (25 ml measuring cylinder) at 15 min intervals in each case and the secreted HCl by titration with a freshly prepared 0.01N NaOH [lacuna] to pH 7 (Dosimat 655 Metrohm).

The stimulation of gastric secretion was effected by continuous infusion of 1 μg/kg (=1.65 ml/h) i.v. of pentagastrin (left femoral vein) about 30 min after the end of the operation (i.e. after determination of 2 preliminary fractions). The substances to be tested were administered intravenously in a 1 ml/kg liquid volume 60 min after the start of continuous pentagastrin infusion.

The body temperature of the animals was kept at a constant 37.8°–38° C. by infrared irradiation and heating pads (automatic, stepless control via rectal temperature sensor).

I claim:
1. A compound of formula I

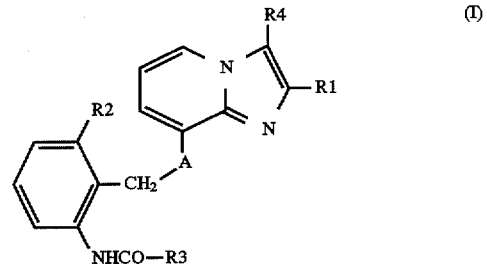

in which
R1 is 1-4C-alkyl,
R2 is 1-4C-alkyl,
R3 is 1-4C-alkoxy-2-4C-alkoxy,
R4 is 1-4C-alkyl or hydroxymethyl and
A is O (oxygen) or NH,
or a salt thereof.

2. A compound of formula I according to claim 1, in which R4 is hydroxymethyl and A is O (oxygen) and R1, R2 and R3 have the meanings indicated in claim 1, or a salt thereof.

3. The compound 8-{2-[(2-Methoxyethoxy)carbonylamino]-6-methylbenzyloxy}-2-methylimidazo[1,2-a]pyridine-3-methanol or a salt thereof.

4. A compound 8-{2-[(2-Methoxyethoxy)carbonylamino] 6-methylbenzylamino}-2-methylimidazo[1,2-a]pyridine-3-methanol or a salt thereof.

5. 8-{2-[(2-Methoxyethoxy)carbonylamino]-6-methylbenzylamino}-2,3-dimethylimidazo[1,2 -a]pyridine or a salt thereof.

6. Process for the preparation of a compound of formula I according to claim 1 or a salt thereof characterized in that
a) compounds of the formula II

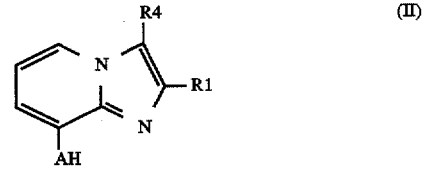

in which R1, R4 and A have the meanings indicated in claim 1, or their salts, are reacted with compounds of the formula III

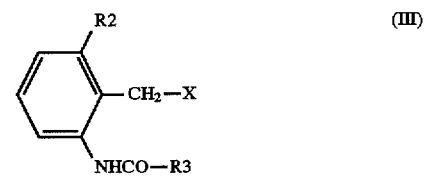

in which R2 and R3 have the meanings indicated in claim 1 and X is a suitable reactive leaving group, or their salts, or in that
b) for the preparation of compounds of the formula I in which R4 is hydroxymethyl, compounds of the formula

IV

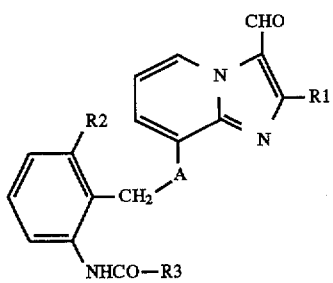

in which R1, R2, R3 and A have the meanings indicated in claim 1, are reduced and optionally, the compounds I obtained according to a) or b) are then converted into their salts, or, optionally, the compounds I are then liberated from salts of the compounds I obtained.

7. A medicament composition comprising a combination of a suitable carrier with a compound according to claim 1 and/or a pharmacologically tolerable salt thereof.

8. In a method of treating a gastrointestinal disease due to hyperacidic condition or Helicobacter pylori by administering an effective amount of active ingredient to a subject afflicted with such disease, the improvement wherein the active ingredient is a compound according to claim 1 and/or a pharmaceutically tolerable salt thereof.

9. In a method for compounding a medicament composition comprising an active ingredient for treating a gastrointestinal disease due to hyperacidic condition or Helicobacter pylori, the improvement wherein the active ingredient is a compound according to claim 1 or a pharmaceutically tolerable salt thereof.

* * * * *

UNITED STATES PATENT AND TRADEMARK OFFICE
CERTIFICATE OF CORRECTION

PATENT NO. : 5,719,161
DATED : February 17, 1998
INVENTOR(S) : RAINER

It is certified that error appears in the above-indentified patent and that said Letters Patent is hereby corrected as shown below:

```
     Column 3, line 49, start a new paragraph and "8-"
should read --2.  8- --.
Column 6, line 2, "of the" should read --of --.
Column 7, line 58, "Metrokm" should read --Metrohm--.
Column 8, line 35, "A" should read --The--; line 38, "5."
should read --5.  The compound--.
Columns 9 and 10, below line 19, insert the following:
--
```

FORMULA SHEET

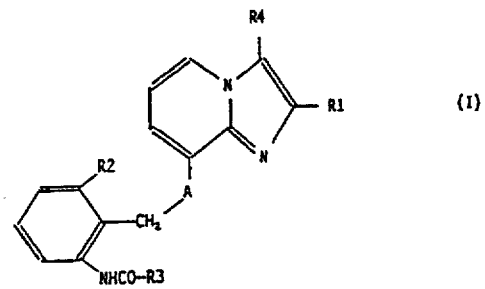

(I)

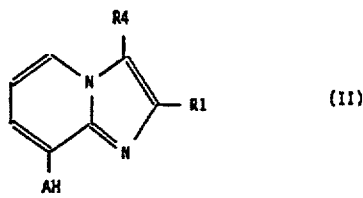

(II)

UNITED STATES PATENT AND TRADEMARK OFFICE
CERTIFICATE OF CORRECTION

PATENT NO. : 5,719,161

DATED : February 17, 1998

INVENTOR(S) : RAINER

It is certified that error appears in the above-indentified patent and that said Letters Patent is hereby corrected as shown below:

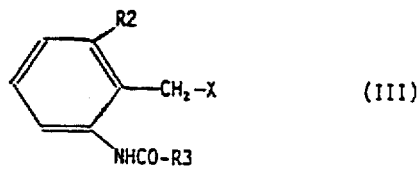

(III)

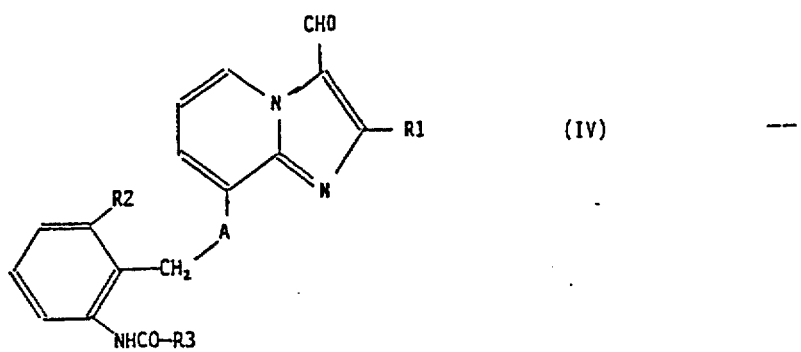

(IV)

Signed and Sealed this

Twenty-first Day of July, 1998

Attest:

BRUCE LEHMAN

Attesting Officer   Commissioner of Patents and Trademarks